United States Patent [19]

Hansen et al.

[11] Patent Number: 5,958,887
[45] Date of Patent: *Sep. 28, 1999

[54] USE OF A HYMENOPTERA VENOM FOR THE MANUFACTURE OF A MEDICAMENT FOR TREATING DNA VIRUS INFECTIONS

[76] Inventors: Michael Hansen, Valmuevej 13, 3390 Hundested; Ole Gyring Nieben, Peblinge Dossering 18, Copenhagen N, both of Denmark

[*] Notice: This patent is subject to a terminal disclaimer.

[21] Appl. No.: 09/102,335

[22] Filed: Jun. 22, 1998

Related U.S. Application Data

[63] Continuation of application No. 08/786,518, Jan. 21, 1997, Pat. No. 5,827,829, which is a continuation of application No. 08/356,336, Jan. 10, 1995, abandoned, which is a continuation of application No. PCT/DK93/00208, Jun. 24, 1992.

[30] Foreign Application Priority Data

Jun. 24, 1992 [DK] Denmark ................................ 0828/92

[51] Int. Cl.$^6$ ........................... A61K 38/00; A61K 39/245
[52] U.S. Cl. ............................... 514/21; 514/12; 514/886; 514/887; 514/931; 514/934; 424/78.07; 424/230.1; 424/231.1; 530/858
[58] Field of Search ............................... 514/21, 12, 886, 514/887, 931, 934; 424/78.07, 230.1, 231.1; 530/858

[56] References Cited

U.S. PATENT DOCUMENTS

| | | | |
|---|---|---|---|
| 3,856,936 | 12/1974 | Vick et al. ................................. | 514/21 |
| 4,370,316 | 1/1983 | Saikawa et al. ........................... | 514/21 |
| 4,444,753 | 4/1984 | Saikawa et al. ........................... | 514/21 |
| 4,822,608 | 4/1989 | Benton et al. ............................. | 514/21 |

FOREIGN PATENT DOCUMENTS 0 504 191 B1  8/1994  European Pat. Off. .

OTHER PUBLICATIONS

Mohanty et al, *Veterinary Virology*, pp. 10–21, Published by Lea & Febiger, Philadelphia, 1981.
Dayan, D. et al., *Acta Tropica* 40:147–153 (1983).
Lu, Gang et al., *J. Immunology* 150(7):2823–2830 (Apr. 1, 1993).
King, Te Piao et al., *J. Allergy Clin. Immunol.* 75:621–8 (1985).
King, Te Piao et al., *J. Allergy Clin. Immunol.* 98:588–600 (1996).
Te Piao King, et al., "Wasp Venom Proteins: Phospholipase $A_1$ and $B^1$," *Archives of Biochemistry and Biophysics*, 230(1) (Apr. 1984), pp. 1–12.
Roy et al., *Biochemical and Biophysical Research Communications* 105(4):1265–1271, Apr. 29, 1982.
Yorist et al., *J. Gen. Virol.* 64:1475–1481, 1983.
Webb et al., *Proc. Natl. Acad. Scit. USA* 87:4961–4965, Jul. 1990.
Baghian et al., *Virology* 196:548–556, 1993.

*Primary Examiner*—Robert J. Hill, Jr.
*Assistant Examiner*—Abdel A. Mohamed
*Attorney, Agent, or Firm*—Darby & Darby

[57] ABSTRACT

The present invention relates to the use of hymenoptera venom or proteinaceous or polypeptide components contained therein in the manufacture of a medicament for treating DNA virus infections, and to a method for treatment of mammalian DNA virus infections which uses hymenoptera venom or proteinaceous or polypeptide components contained therein.

17 Claims, No Drawings

USE OF A HYMENOPTERA VENOM FOR THE MANUFACTURE OF A MEDICAMENT FOR TREATING DNA VIRUS INFECTIONS

This is a continuation of application Ser. No. 08/786,518, filed Jan. 21, 1997, now U.S. Pat. No. 5,827,829 which is a continuation of application Ser. No. 08/356,336 filed Jan. 10, 1995, now abandoned which is a con of PCT appln DK93/00208, filed Jun. 24, 1992. Each of these prior applications is hereby incorporated herein by reference, in its entirety.

FIELD OF THE INVENTION

The present invention relates to the use of a hymenoptera venom or a proteinaceous or polypeptide component contained therein in the manufacture of a medicament for treating DNA virus infections, and to a method for the treatment of DNA virus infections which uses a hymenoptera venom or a proteinaceous or polypeptide component contained therein.

BACKGROUND OF THE INVENTION

The use of venoms of various origin as components in medicaments is of long standing. Dilute solutions of different hymenoptera venoms are used for injection in immune therapy for patients who are allergic to the stings of the insects. Also, dilute solutions of the venoms are used as allergens by application to the skin in testing for allergy. In recent time, bee venom has been used in the management of certain types of bronchial asthma (Kirusha V P et al., Ter. Arkh. 60 (1988), 81–84: Organisation and Results of Treatment Of Bronchial Asthma Patients in the District of Vologda) and in the management of syringomyelia and various related conditions (Ludyanskii E A, Zh. Nevropatol. Psikhiatr. 91 (1991), 102–03. Other diseases in which bee venom has been used or tested are multiple sclerosis, arthritis and diseases which influence the coagulation properties of the blood. Other hymenoptera venoms have been suggested for treatment and prophylaxis of gingivitis. WO 91/08753 (to Gesellschaft für Strahlen- und Umweltforschung MBH) discloses the use of an agent comprising at least one hymenoptera venom or a component thereof in the treatment of retroviral infections, in particular HIV infection, in a mammal. U.S. Pat. No. 4,822,608 (to Vespa Laboratories, Inc.) discloses the use of at least one hymenoptera venom or a component thereof in combination with an antibiotic agent in the treatment of mammalian infections, including bacterial, viral, and cancerous infections.

Combating virus infections is important not only in mammals. Thus, in poultry breeding virus infections may impart considerable losses.

One of the most promising agents for the treatment of virus infections caused i.a. by herpes simplex virus types 1 and 2 and varicella-zoster virus is known as acyclovir (Whitley R J, et al., N Engl J Med 327 (1992), 782–89: Acyclovir: A Decade Later). In herpes genitalis, oral or intravenous therapy with acyclovir which are considered more effective than topical application of acyclovir does not reduce the frequency of recurrences. Although the indications for acyclovir therapy expand, the appearance of isolates resistant to acyclovir underscores the need for continued development of new agents with new mechanisms of action.

Accordingly, one object of the present invention is to provide an improved medicament and method for the treatment of DNA virus infections, preferably in mammals and birds, more preferred in mammals, which is based on a hymenoptera venom or an active proteinaceous or polypeptide component contained therein or mixtures thereof.

Another object of the invention is to provide such a medicament and a method wherein the hymenoptera venom or component thereof is selected from the group consisting essentially of honey bee venom, bumble bee venom, yellow jacket venom, bald faced hornet venom, active proteinaceous components of said venoms, active polypeptide components of said venoms, and mixtures thereof.

SUMMARY OF THE INVENTION

Surprisingly, it has turned out that when a dilute aqueous solution of a hymenoptera venom is applied topically to human skin afflicted by a DNA virus infection a reduction of pain, an accellerated recovery, and a reduction in the number of recurrences is achieved.

Thus, in its broadest aspect the present invention relates to the use of a subtoxic amount of a hymenoptera venom or a proteinaceous or a polypeptide component contained therein or mixtures thereof in the manufacture of a medicament for treating DNA virus infections, preferably in mammals and birds, more preferred in mammals and to a method for the treatment of such DNA virus infections which comprises administering to an individual in need of such treatment a subtoxic amount of a hymenoptera venom or a proteinaceous or a polypeptide component contained therein or a mixture thereof.

In one preferred embodiment, the present invention relates to the use of an agent selected from the group consisting essentially of honey bee venom, bumble bee venom, yellow jacket venom, bald faced hornet venom, active proteinaceous components of said venoms, active polypeptide components of said venoms, and mixtures thereof in the manufacture of a medicament for treating DNA virus infections.

In another preferred embodiment, the present invention relates to the use of an agent selected from the group consisting essentially of honey bee venom, bumble bee venom, yellow jacket venom, bald faced hornet venom, active proteinaceous components of said venoms, active polypeptide components of said venoms, and mixtures thereof in the manufacture of a medicament for treating DNA virus infections, preferably in mammals and birds, more preferred in mammals.

In another preferred embodiment, the present invention relates to the use of an agent selected from the group consisting essentially of honey bee venom, bumble bee venom, yellow jacket venom, bald faced hornet venom, active proteinaceous components of said venoms, active polypeptide components of said venoms, and mixtures thereof in the manufacture of a medicament for treating avian DNA virus infections.

In another preferred embodiment, the present invention relates to the manufacture of a medicament for treating herpes virus infections.

In another preferred embodiment, the present invention relates to the manufacture of a medicament for treating herpes simplex virus type 1 infections.

In another preferred embodiment, the present invention relates to the manufacture of a medicament for treating herpes simplex virus type 2 infections.

In another preferred embodiment, the present invention relates to the manufacture of a medicament for treating varicella infections.

In another preferred embodiments the present invention relates to the manufacture of a medicament for treating herpes zoster infections.

In another preferred embodiment, the present invention relates to the manufacture of a medicament for treating cytomegalovirus infections.

In another preferred embodiment, the present invention relates to the manufacture of a medicament for treating papilloma virus infections.

In another preferred embodiment, the present invention relates to a method for the treatment of DNA virus infections which comprises administering to an individual in need of such treatment a subtoxic amount of an agent selected from the group consisting of honey bee venom, bumble bee venom, yellow jacket venom, bald faced hornet venom, active proteinaceous components of said venoms, active polypeptide components of said venoms, and mixtures thereof.

In another preferred embodiment, the present invention relates to a method for the treatment of herpes simplex type 1 infections.

In another preferred embodiment, the present invention relates to a method for the treatment of herpes simplex type 2 infections.

In another preferred embodiment, the present invention relates to a method for the treatment of varicella infections.

In another preferred embodiment, the present invention relates to a method for the treatment of herpes zoster infections.

In another preferred embodiment, the present invention relates to a method for the treatment of cytomegalovirus infections.

In another preferred embodiment, the present invention relates to a method for the treatment of papilloma infections.

DETAILED DESCRIPTION OF THE INVENTION

The results reported in the examples indicate that the medicament and the method according to the present invention provides an improved therapy of DNA virus infections. A turn to the better is seen in three important parameters: the pain is reduced, healing is faster, and there are fewer recurrencies.

The daily dosage of the active agents of this invention is determined according to the condition of the individual to be treated by those skilled in the art. The amount of agent to be administered will depend i.a. on the specific agent in question, the condition to be treated, the particular mode of administration, and on the age, health, sex, bodyweight, and diet of the individual to be treated.

Compositions for administering the active agents according to the invention may have either a local or a systemic effect. In such compositions, the active agents according to the invention may be combined with the carriers, adjuvants, and vehicles usually employed in the art.

Solutions for topical application of an active agent according to the invention can be made in which water is the only solvent. Alternatively, the solvent can be a mixture of water and one or more pharmaceutically acceptable organic solvents.

Other compositions suitable for topical application can be provided in the form of creams, ointments, gels, or powders.

A systemic effect can be achieved by injection or infusion of sterile solutions of the active agents according to the invention the solutions being prepared according to the known art. Also, a systemic effect can be achieved by inhalation or by nasal administration of a powder or an aerosol containing the active agent.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

Treatment of Herpes Labialis

An open trial a was performed using wasp venom (from Vespula vulgaris, obtained from Allergologisk Laboratorium A/S, DK-2970 Hørsholm, Denmark). In the trial, the venom was used in the form of an aqueous solution which contained 120 μg/ml of the venom and 0.3 mg/ml of human albumin. 18 patients with recurrent herpes labialis were included in the the trial.

The solution was applied topically on the day when the outburst was observed and on the following day. The application was performed as follows: The whole afflicted area was moistened with the solution and allowed to dry. After 10 minutes, 20 minutes, and 30 minutes the afflicted area was again moistened with the solution and allowed to dry. It is estimated that approximately 0.01 ml of the solution was applied to each square centimeter of the afflicted area in each stage of the application.

Before the trial, the time from the outburst of symptoms until crust formation took place was seven days (median). In the trial, the time until crust formation took place was two days (median). Already a few hours after the first application of the solution the patients felt a reduction in pain. Before the trial, the patients had had an average of six episodes (a minimum of three, a maximum of ten) of herpes labialis per year. During a six month observation period following the treatment the average number of recurrences was one (a minimum of zero, a maximum of three).

One patient had an outburst of herpes on the upper lip and simultaneously an outburst on the lower lip which looked very similar to the outburst on the upper lip. The solution was only applied to the upper lip where crust formation took place after two days. On the lower lip which was left untreated crust formation only took place after five days. The results are reported in Table 1

TABLE 1

|  | No of patients | Days until crusting **) | No. of recurrences per year **) |
|---|---|---|---|
| Before treatment with wasp venom | 18 | 7 (3–21) | 6 (3–10) |
| After treatment with wasp venom | 17*) | 2 (1–5) | 1 (0–3) |

*) One patient was not followed.
**) Medians are reported figures in parenthesis are ranges.

The above findings indicate that treatment with the solution containing wasp venom causes a faster healing of herpes labialis lesions and significantly reduces the number of recurrences.

EXAMPLE 2

Treatment of Herpes Genitalis

Three male patients with a history of herpes genitalis recurring at least six times per year were treated by topical application of the solution mentioned in Example 1 on the day of the outburst of a new episode and on the following day. The application was performed in four stages as described in Example 1. The lesions had a faster healing than usual and less pain was experienced. After one year, two of the patients had had no recurrencies. One and a half year after the treatment the third patient had only had two recurrencies which were abortive episodes with formation of erythema but no crust formation.

We claim:

1. A method for the treatment of DNA virus infections which comprises administering to a subject in need thereof a composition comprising a therapeutically active amount of an agent selected from the group consisting of a hymenoptera venom, an active proteinaceous or polypeptide component contained therein and a mixture thereof;

said venom or proteinaceous or polypeptide component thereof having at least one of the following properties: (i) reducing pain associated with said DNA virus infection, (ii) promoting faster healing; (iii) reducing the number of infection recurrencies; (iv) inhibiting or reducing the viral load or replication; and (v) reducing inflammation.

2. A method according to claim 1 wherein the agent is selected from the group consisting of honey bee venom, bumble bee venom, yellow jacket venom, bald faced hornet venom, an active proteinaceous or polypeptide component contained in said venoms, and a mixture thereof.

3. A method according to claim 1 for the treatment of herpes virus infections.

4. A method according to claim 1 for the treatment of herpes simplex type 1 virus infections.

5. A method according to claim 1 for the treatment of herpes simplex type 2 virus infections.

6. A method according to claim 1 for the treatment of varicella virus infections.

7. A method according to claim 1 for the treatment of herpes zoster virus infections.

8. A method according to claim 1 for the treatment of cytomegalovirus infections.

9. A method according to claim 1 for the treatment of papilloma virus infections.

10. A method of claim 1, wherein said subject is a mammal.

11. A method for the treatment of DNA virus infections which comprises administering to a subject in need thereof a composition comprising a therapeutically active amount of an agent selected from the group consisting of a hymenoptera venom, an active proteinaceous or polypeptide component contained therein and a mixture thereof;

said venom or proteinaceous or polypeptide component thereof having at least one of the following properties: (i) reducing pain associated with said DNA virus infection, (ii) promoting faster healing; and (iii) reducing the number of infection recurrencies.

12. A method according to claim 11 wherein the agent is selected from the group consisting of honey bee venom, bumble bee venom, yellow jacket venom, bald faced hornet venom, an active proteinaceous or polypeptide component contained in said venoms, and a mixture thereof.

13. A method of claim 11, wherein said subject is a mammal.

14. A method for alleviating at least one symptom of a DNA virus infection comprising administering to a subject in need thereof a composition comprising a therapeutically active amount of an agent selected from the group consisting of a hymenoptera venom, an active proteinaceous or polypeptide component contained therein and a mixture thereof.

15. A method according to claim 14 wherein the agent is selected from the group consisting of honey bee venom, bumble bee venom, yellow jacket venom, bald faced hornet venom, an active proteinaceous or polypeptide component contained in said venoms, and a mixture thereof.

16. A method of claim 14, wherein said subject is a mammal.

17. A method for treating a DNA virus infection comprising topically administering to a mammal in need of said treatment a composition comprising a therapeutically active amount of an agent selected from the group consisting of a hymenoptera venom, an active proteinaceous or polypeptide component contained therein and a mixture thereof;

said venom or proteinaceous or polypeptide component thereof having at least one of the following properties: (i) reducing pain associated with said viral infection, (ii) promoting faster healing; (iii) reducing the number of infection recurrencies; (iv) inhibiting or reducing the viral load or replication; and (v) reducing inflammation.

* * * * *

UNITED STATES PATENT AND TRADEMARK OFFICE
CERTIFICATE OF CORRECTION

PATENT NO. : 5,958,887
DATED : September 28, 1999
INVENTOR(S) : Michael Hansen and Ole Gyring Nieben It is certified that errors appear in the above-identified patent and that said Letters Patent is hereby corrected as shown below:

Foremost page, [63] Related U.S. Application Data: please change

"Jun. 24, 1992" to -- Jun. 24, 1993 --.

Signed and Sealed this

Twenty-ninth Day of May, 2001

Attest:

NICHOLAS P. GODICI

*Attesting Officer*   *Acting Director of the United States Patent and Trademark Office*